(12) United States Patent
Ivosevic et al.

(10) Patent No.: US 11,077,976 B2
(45) Date of Patent: Aug. 3, 2021

(54) PIERCING MEMBER FOR CONTAINER ACCESS DEVICE

(71) Applicant: Becton Dickinson and Company Ltd., Dun Laoghaire (IE)

(72) Inventors: Milan Ivosevic, Kinnelon, NJ (US); Paul Paia Marici, Piscataway, NJ (US)

(73) Assignee: Becton Dickinson and Company Ltd., Dun Laoghaire (IE)

( * ) Notice: Subject to any disclaimer, the term of this patent is extended or adjusted under 35 U.S.C. 154(b) by 559 days.

(21) Appl. No.: 15/889,726

(22) Filed: Feb. 6, 2018

(65) Prior Publication Data

US 2018/0162578 A1 Jun. 14, 2018

Related U.S. Application Data

(62) Division of application No. 14/492,305, filed on Sep. 22, 2014, now Pat. No. 9,919,826.

(60) Provisional application No. 61/881,148, filed on Sep. 23, 2013.

(51) Int. Cl.
| | |
|---|---|
| *A61J 1/20* | (2006.01) |
| *A61M 5/32* | (2006.01) |
| *A61M 39/04* | (2006.01) |
| *B65B 69/00* | (2006.01) |
| *A61M 5/162* | (2006.01) |

(52) U.S. Cl.
CPC ......... *B65B 69/0041* (2013.01); *A61J 1/2096* (2013.01); *A61M 5/1626* (2013.01); *A61M 5/329* (2013.01); *A61M 5/3286* (2013.01); *A61J 1/201* (2015.05); *A61J 1/2075* (2015.05); *A61M 5/162* (2013.01); *A61M 39/04* (2013.01); *A61M 2205/195* (2013.01)

(58) Field of Classification Search
CPC ........ A61J 1/201; A61J 1/2075; A61J 1/2096; A61M 39/04; A61M 5/162; A61M 5/1626; A61M 5/158; A61M 5/32; A61M 5/3286; A61M 5/3268; A61M 5/329; A61M 2205/195
See application file for complete search history.

(56) References Cited

U.S. PATENT DOCUMENTS

| 4,826,492 A | 5/1989 | Magasi |
|---|---|---|
| 5,478,328 A | 12/1995 | Silverman et al. |

(Continued)

FOREIGN PATENT DOCUMENTS

| CN | 102985050 A | 3/2013 |
|---|---|---|
| CN | 103153260 A | 6/2013 |

(Continued)

*Primary Examiner* — Leslie R Deak
(74) *Attorney, Agent, or Firm* — The Webb Law Firm

(57) ABSTRACT

A device for transferring fluids includes a piercing member having a distal end and a proximal end and defines a longitudinal fluid channel. An opening is positioned at the distal end of the piercing member with the opening in fluid communication with the longitudinal fluid channel. Further, a sleeve having a proximal end and a distal end includes an extended position where the sleeve surrounds the piercing member and a retracted position where the sleeve is retracted from the distal end of the piercing member. The sleeve defines an opening at the distal end of the sleeve with a gap defined between the retractable sleeve and the piercing member.

3 Claims, 20 Drawing Sheets

(56) References Cited

U.S. PATENT DOCUMENTS

| | | | |
|---|---|---|---|
| 6,139,534 A * | 10/2000 | Niedospial, Jr. | A61J 1/2096 604/403 |
| 6,253,804 B1 * | 7/2001 | Safabash | A61J 1/2096 141/311 R |
| 7,150,735 B2 | 12/2006 | Hickle | |
| 7,468,055 B2 * | 12/2008 | Prais | A61M 5/3202 604/272 |
| 8,454,573 B2 | 6/2013 | Wyatt et al. | |
| 8,545,476 B2 | 10/2013 | Ariagno et al. | |
| 2003/0229330 A1 | 12/2003 | Hickle | |
| 2007/0106244 A1 | 5/2007 | Mosler et al. | |
| 2009/0057258 A1 | 3/2009 | Tornqvist | |
| 2012/0053555 A1 | 3/2012 | Ariagno et al. | |
| 2012/0095404 A1 * | 4/2012 | Massengale | A61B 8/481 604/164.01 |
| 2013/0079744 A1 | 3/2013 | Okiyama et al. | |
| 2013/0228239 A1 | 9/2013 | Cederschiold | |

FOREIGN PATENT DOCUMENTS

| | | |
|---|---|---|
| EP | 2095841 A1 | 9/2009 |
| EP | 2308452 A1 | 4/2011 |
| JP | S53125968 U | 10/1978 |
| JP | 11019186 A | 1/1999 |
| JP | H1119186 A | 1/1999 |
| JP | 2005525880 A | 9/2005 |
| WO | 2013130971 A1 | 9/2013 |

\* cited by examiner

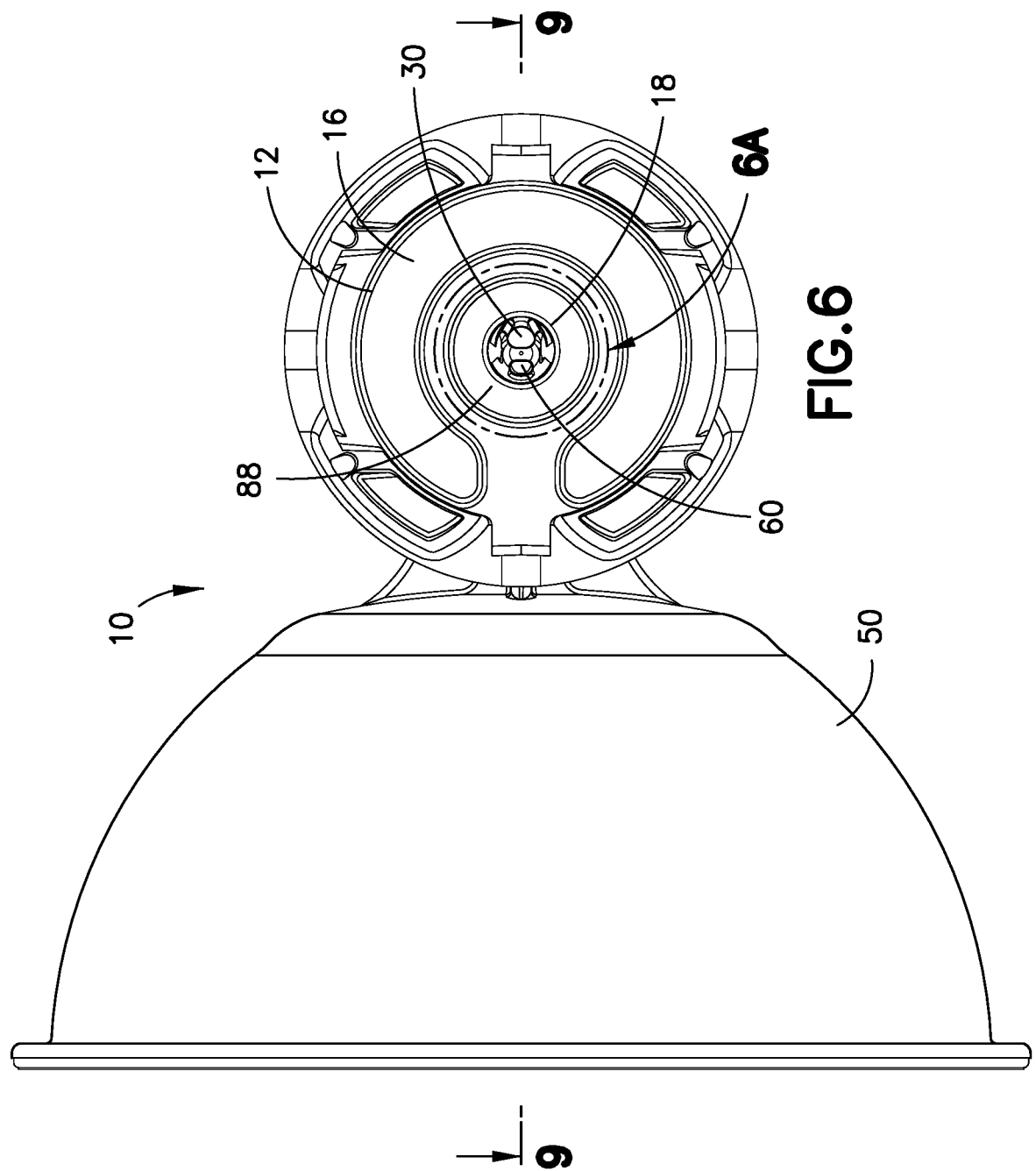

PIERCING MEMBER FOR CONTAINER ACCESS DEVICE

CROSS-REFERENCE TO RELATED APPLICATION

This application is a divisional of U.S. patent application Ser. No. 14/492,305, filed on Sep. 22, 2014, which claims priority to U.S. Provisional Application Ser. No. 61/881,148, filed Sep. 23, 2013, each of which are hereby incorporated by reference in their entirety.

BACKGROUND OF THE INVENTION

Field of the Invention

The present invention relates to a device for transferring a fluid to or from a fluid container have a sealing member.

Description of Related Art

Medical drugs and solvents are often supplied in glass or plastic containers, such as vials, bottles, or bags, which are sealed by a rubber, plastic or elastomeric bung, stopper, membrane, or puncturable cap. Such sealing members prevent deterioration or contamination of the drug, allow the contents of a container to be mixed by shaking, and prevent the contents of the container from leaking out and contaminating the surroundings. A cannula or a hollow spike comprising a flow channel and an opening that communicates with the flow channel is usually inserted through such a sealing member to supply fluids to the container and to withdraw fluid therefrom.

Conventional devices used for accessing the containers utilize a piercing member that penetrates the sealing member of a container and defines an opening at a distal end of the piercing member. Typically, after the piercing member accesses the vial, the vial is inverted to withdraw the medicament from the container. Once the contents of the fluid container have drained to a level just under the outermost edge of the opening of the piercing member, no more fluid will be able to drain from the fluid container unless the piercing member is withdrawn slightly. Thus, often times the last few drops of the medicament (which may be very expensive and/or toxic) are not fully removed from the container, which results in waste and requires cleaning/disposal of the container. If the piercing member is retracted through the sealing member of the container to remove the remaining medicament in the container, toxic drug or medicament may leak out and contaminate the surrounding environment during such a procedure and non-filtered air containing undesirable particles such as dust, pollen, or bacteria may be drawn into the piercing member and contaminate the medicament therein. Accordingly, many conventional devices will be locked to the container or vial after the piercing member fully enters the vial. In some cases, containers are provided with an extra amount of the drug that is to be withdrawn to allow for the fact that not all of the drug will be withdrawn from the container. A user is then able to withdraw the recommended number of doses from the container, but doing so will increase the cost of each container of medical fluid, increase waste, and make cleaning or disposal of the container more complex. As sealing members are available in a wide variety of configurations, sizes, and thicknesses, designing a spike that is suitable for use with a plurality of different sealing members while optimizing the use of the drug in the vial in a safe and convenient manner is difficult.

U.S. Publication No. 2009/0057258 to Tornqvist discloses a device for transferring fluid to or from a fluid container having a sealing member. In the embodiment shown in FIGS. 3 and 4, a device includes a tightly fitting elastic retracted sleeve to at least partially cover and seal an opening in the piercing member before the device is inserted into a fluid container.

SUMMARY OF THE INVENTION

In one embodiment, a device for transferring fluids includes a piercing member having a distal end and a proximal end and defines a longitudinal fluid channel. An opening is positioned at the distal end of the piercing member with the opening in fluid communication with the longitudinal fluid channel. Further, a sleeve having a proximal end and a distal end includes an extended position where the sleeve surrounds the piercing member and a retracted position where the sleeve is retracted from the distal end of the piercing member. The sleeve defines an opening at the distal end of the sleeve with a gap defined between the retractable sleeve and the piercing member.

The piercing member may define a longitudinal vent channel and a second opening at the distal end of the piercing member, with the device further comprising a body extending from the proximal end of the piercing member and the body including a first connecting portion configured to receiving a mating connector and a second connecting portion configured to secure the body to a container. The device may include a pressure equalization arrangement in fluid communication with the longitudinal vent channel of the piercing member. The proximal end of the piercing member may be sealed with a proximal end of the retractable sleeve and the gap between the piercing member and the retractable sleeve may extend from the seal between the proximal end of the piercing member and the proximal end of the retractable sleeve to the distal end of the piercing member. The piercing member may have a larger cross-section at the proximal end to provide the seal between the proximal end of the retractable sleeve and the proximal end of the piercing member. A portion of the proximal end of the retractable sleeve may be thicker than a remaining portion of the retractable sleeve to provide the seal between the proximal end of the retractable sleeve and the proximal end of the piercing member.

The retractable sleeve may include a lip extending outwardly from the proximal end. The device may include a body extending outwardly from the proximal end of the piercing member. The body may define a recess for accommodating the proximal end of the retractable sleeve. The opening of the piercing member may extend longitudinally from the distal end of the piercing member. A length of the opening of the piercing member in a direction extending from the proximal end of the piercing member to the distal end of the piercing member may ensure that at least a portion of the opening of the piercing member is located adjacent an innermost side of a sealing member of a fluid container when the piercing member has penetrated the sealing member. The piercing member may be cylindrical with a pointed tip at the distal end. The piercing member may include at least one flat portion defining a planar surface. The sleeve may be made of an elastomeric material. The piercing member may define a longitudinal vent channel in fluid communication with a second opening in the distal end of the piercing member with at least one of the vent channel and fluid channel having a non-circular cross-section. At least one of the vent channel and fluid channel may have an oval-shaped cross-section.

In another embodiment, a device for transferring fluids includes a body having a first side and a second side, a piercing member extending from the second side of the body, with the piercing member having a distal end and a proximal end and defining a longitudinal fluid channel, and at least one opening positioned at the distal end of the piercing member. The at least one opening is in fluid communication with the longitudinal fluid channel, with the piercing member including at least one flat portion.

The piercing member may define a longitudinal vent channel, and the piercing member may include first and second flat portions positioned circumferentially between the longitudinal vent channel and the longitudinal fluid channel, with the first flat portion positioned opposite the second flat portion. The first and second flat portions may be configured to reduce a penetration force required to pierce a sealing member of a fluid container relative to a piercing member not having the first and second flat portions.

The device may include a body extending from the proximal end of the piercing member and define a longitudinal fluid channel in fluid communication with the longitudinal fluid channel of the piercing member. A proximal end of the piercing member is sealed with a proximal end of the retractable sleeve and the gap between the piercing member and the retractable sleeve may extend from the seal between the proximal end of the piercing member and the proximal end of the retractable sleeve to the distal end of the piercing member. The piercing member may have a larger cross-section at the proximal end to provide the seal between the proximal end of the retractable sleeve and the proximal end of the piercing member. A portion of the proximal end of the retractable sleeve may be thicker than a remaining portion of the retractable sleeve to provide the seal between the proximal end of the retractable sleeve and the proximal end of the piercing member. The retractable sleeve may comprise a lip extending outwardly from at least one of the proximal and the distal ends. The device may include a body extending outwardly from the proximal end of the piercing member with the body defining a recess for accommodating the proximal end of the retractable sleeve. The gap may define a distance from an inner surface of the sleeve to an outer surface of the piercing member that is constant. The at least one opening may extend longitudinally from the distal end of the piercing member.

Further, a length of the at least one opening in a direction extending from the proximal end of the piercing member to the distal end of the piercing member may ensure that at least a portion of the opening is located adjacent an innermost side of a sealing member of a fluid container when the piercing member has penetrated the sealing member. The piercing member may be cylindrical with a pointed tip at the distal end. The piercing member may comprise at least one flat side and the retractable sleeve may be made of an elastomeric material, such as rubber. The piercing member may define a longitudinal vent channel in fluid communication with a second opening in the distal end of the piercing member. At least one of the vent channel and fluid channel may have a semi-circular cross-section.

In another embodiment, a device for transferring a fluid to or from a fluid container includes a body having a first side and a second side and a piercing member extending from the second side of the body. The piercing member has a distal end and a proximal end and defines a longitudinal fluid channel. At least one opening is positioned at the distal end of the piercing member with the at least one opening in fluid communication with the longitudinal fluid channel to allow fluid to flow into to or out of the fluid container. The piercing member includes at least one flat portion.

The piercing member may define a longitudinal vent channel, and the piercing member may include first and second flat portions positioned circumferentially between the longitudinal vent channel and the longitudinal fluid channel with the first flat portion positioned opposite the second flat portion. The first and second flat portions are configured to reduce a penetration force required to pierce a sealing member of a fluid container relative to a piercing member not having the first and second flat portions.

BRIEF DESCRIPTION OF THE DRAWINGS

FIG. 6 is a bottom view of the device of FIG. 1 according to one embodiment of the present invention, showing the device with a sleeve removed.

DETAILED DESCRIPTION

Figure 1:
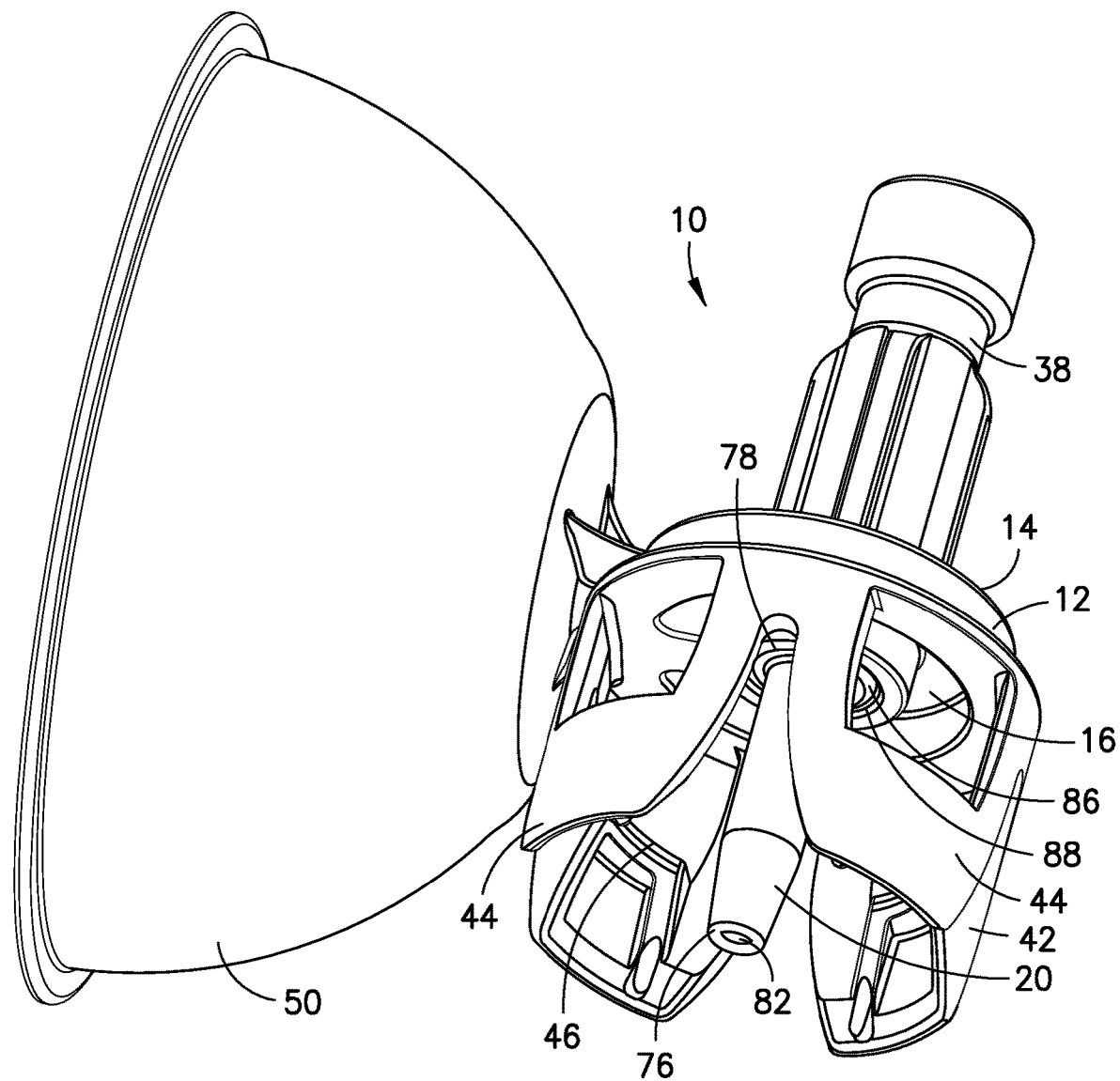
FIG. 1 is a perspective view of a container access device according to one embodiment of the present invention.
Figure 2:
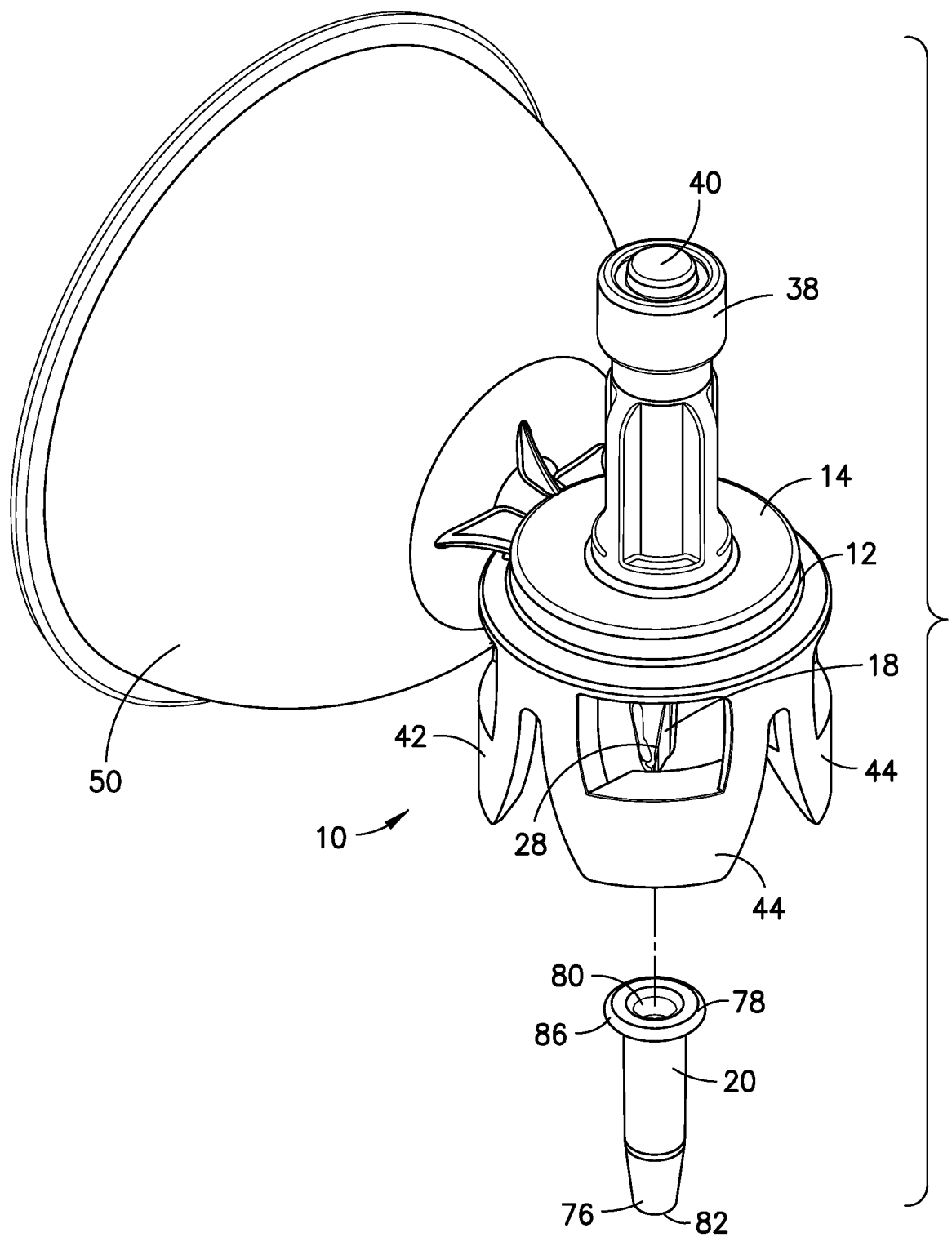
FIG. 2 is an exploded front view of the device of FIG. 1 according to one embodiment of the present invention.
Figure 3:
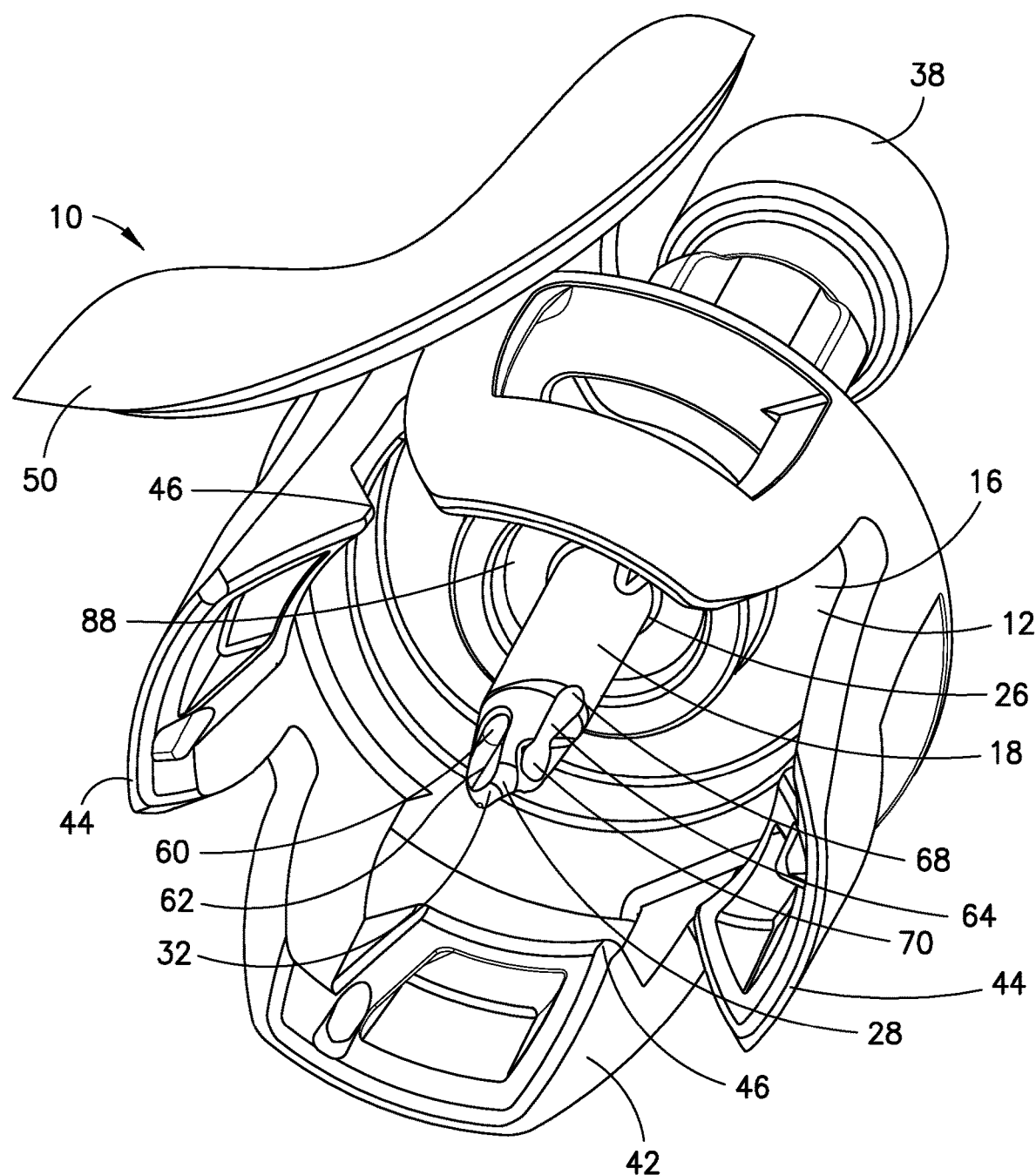
FIG. 3 is a bottom, left-side perspective view of the device of FIG. 1 according to one embodiment of the present invention, showing the device with a sleeve removed.
Figure 4:
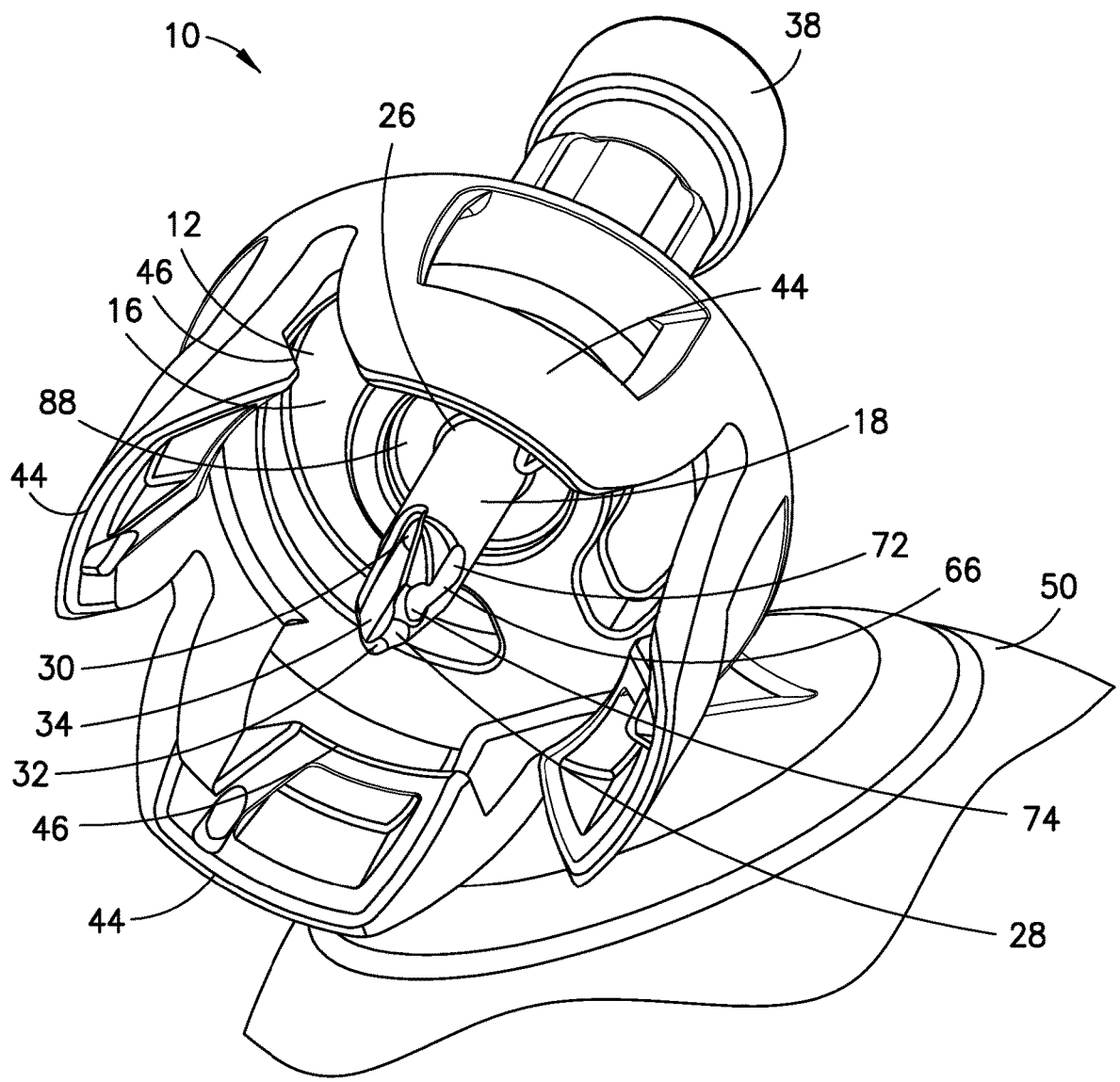
FIG. 4 is a bottom, right-side perspective view of the device of FIG. 1 according to one embodiment of the present invention, showing the device with a sleeve removed.
Figure 5:
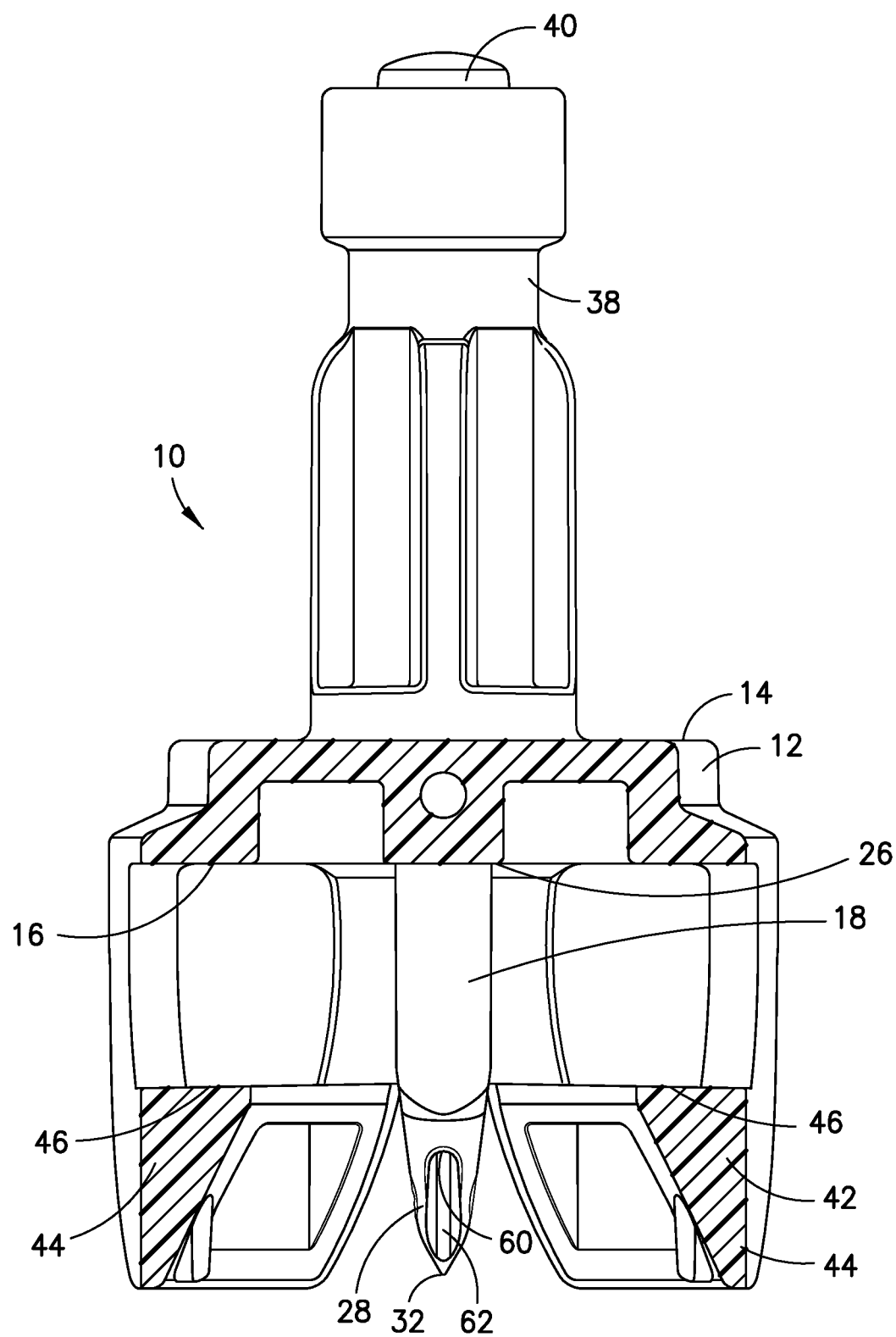
FIG. 5 is a left-side cross-sectional view of the device of FIG. 1 according to one embodiment of the present invention, showing the device with a sleeve removed.
Figure 6A:
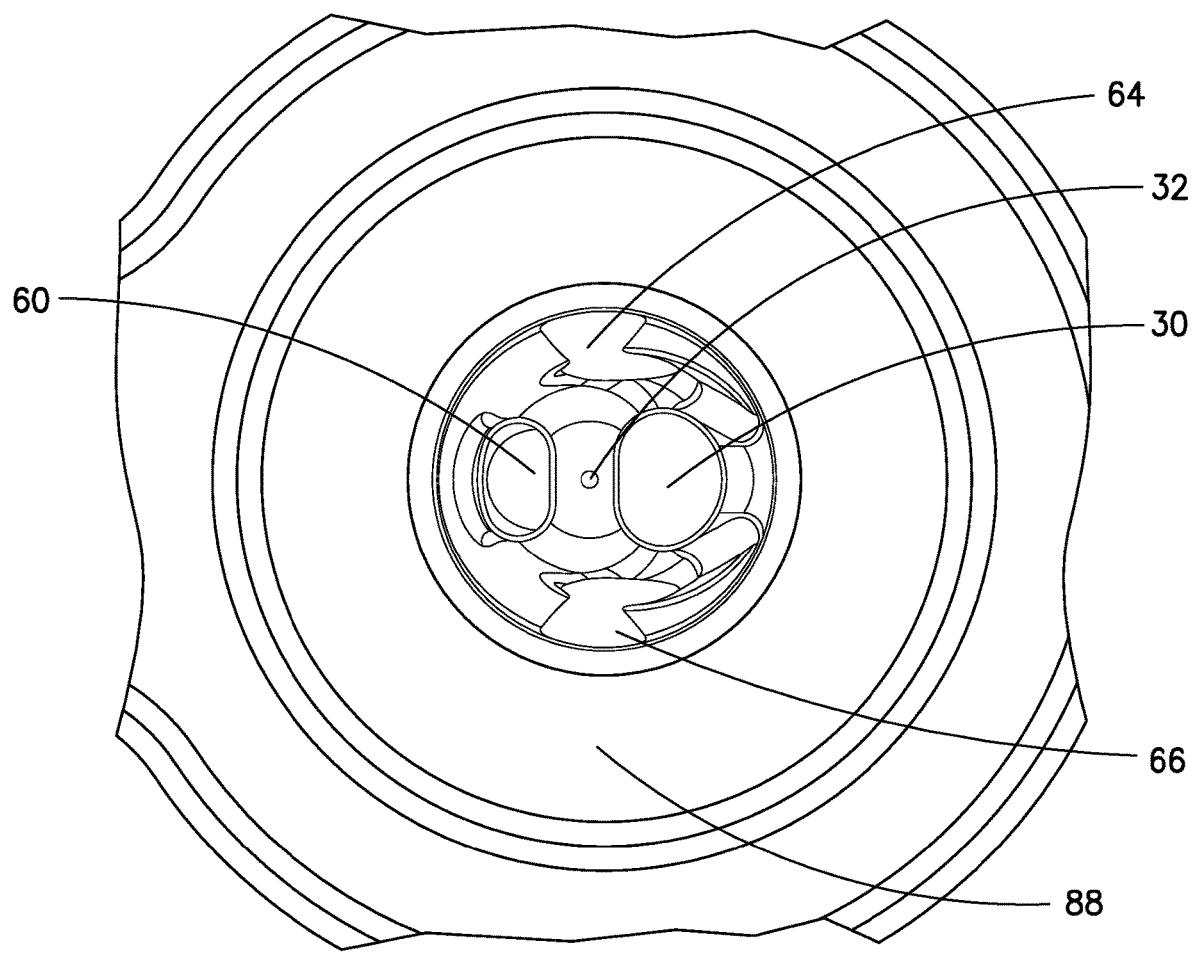
FIG. 6A is an enlarged view of the area indicated in FIG. 6 according to one embodiment of the present invention.
Figure 7:
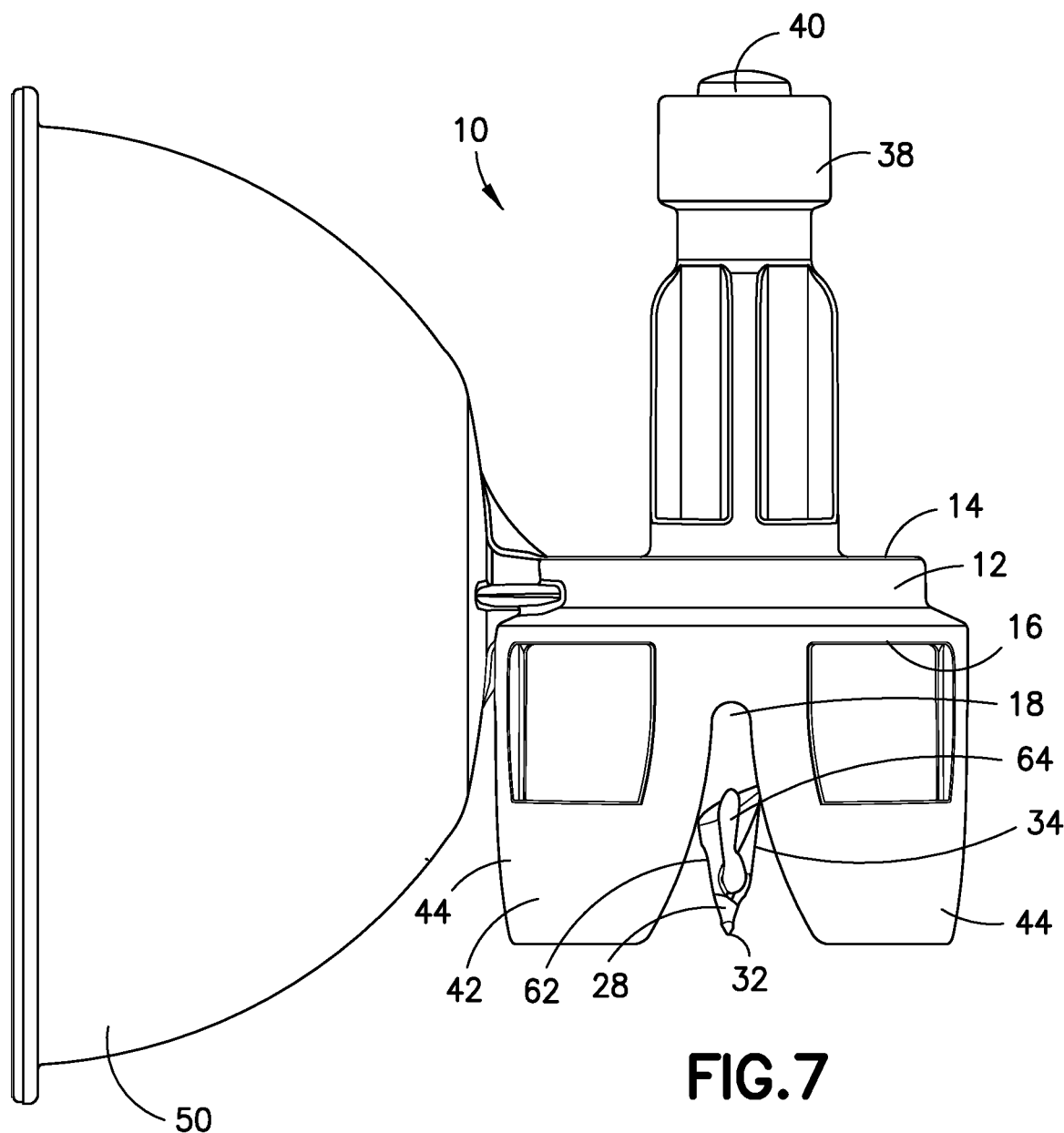
FIG. 7 is a left-side view of the device of FIG. 1 according to one embodiment of the present invention, showing the device with a sleeve removed.
Figure 8:
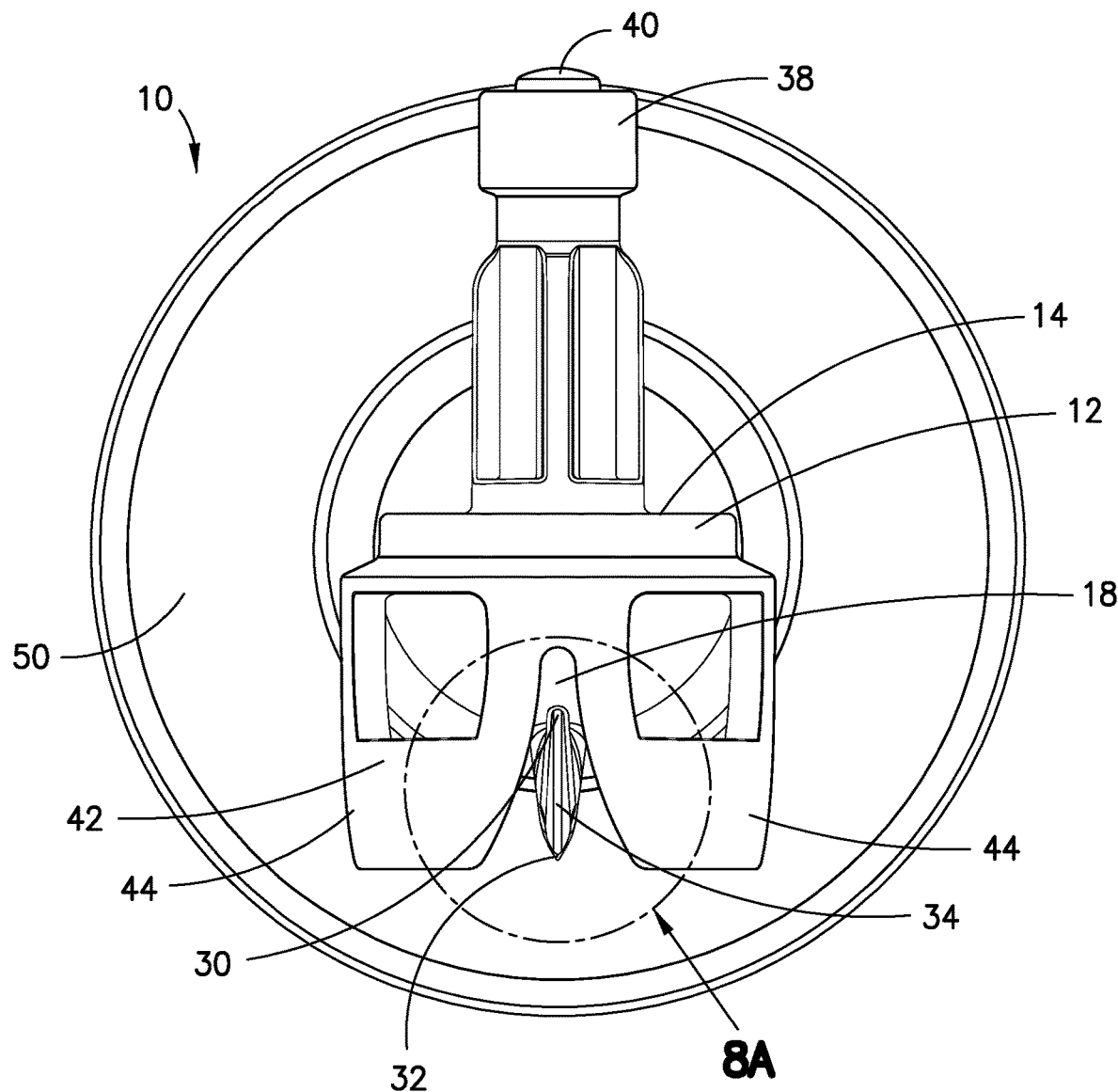
FIG. 8 is a rear view of the device of FIG. 1 according to one embodiment of the present invention, showing the device with a sleeve removed.
Figure 8A:
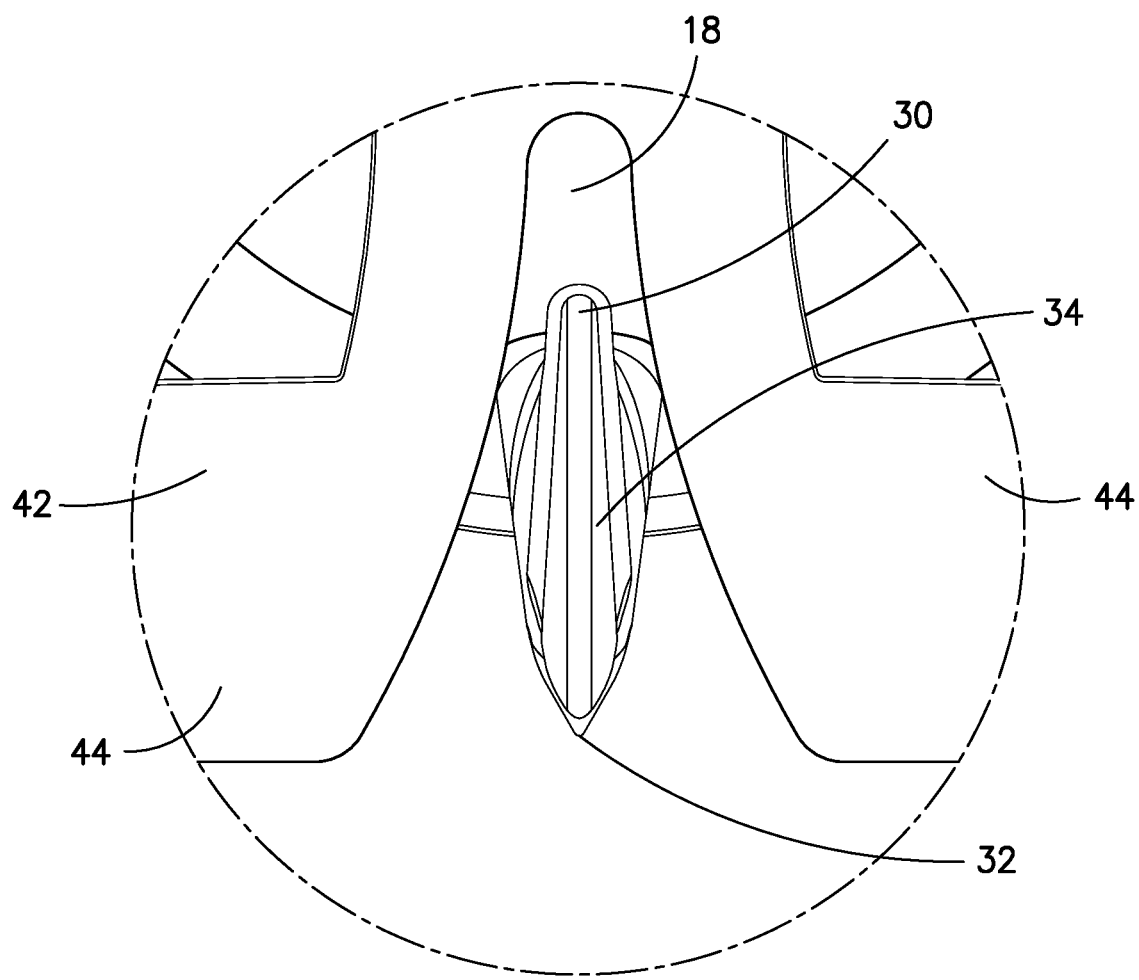
FIG. 8A is an enlarged view of the area indicated in FIG. 8 according to one embodiment of the present invention.

For purposes of the description hereinafter, the terms such as "end", "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. Further, it is to be understood that the invention may assume various alternative variations and step sequences, except where expressly specified to the contrary.

Figure 9:
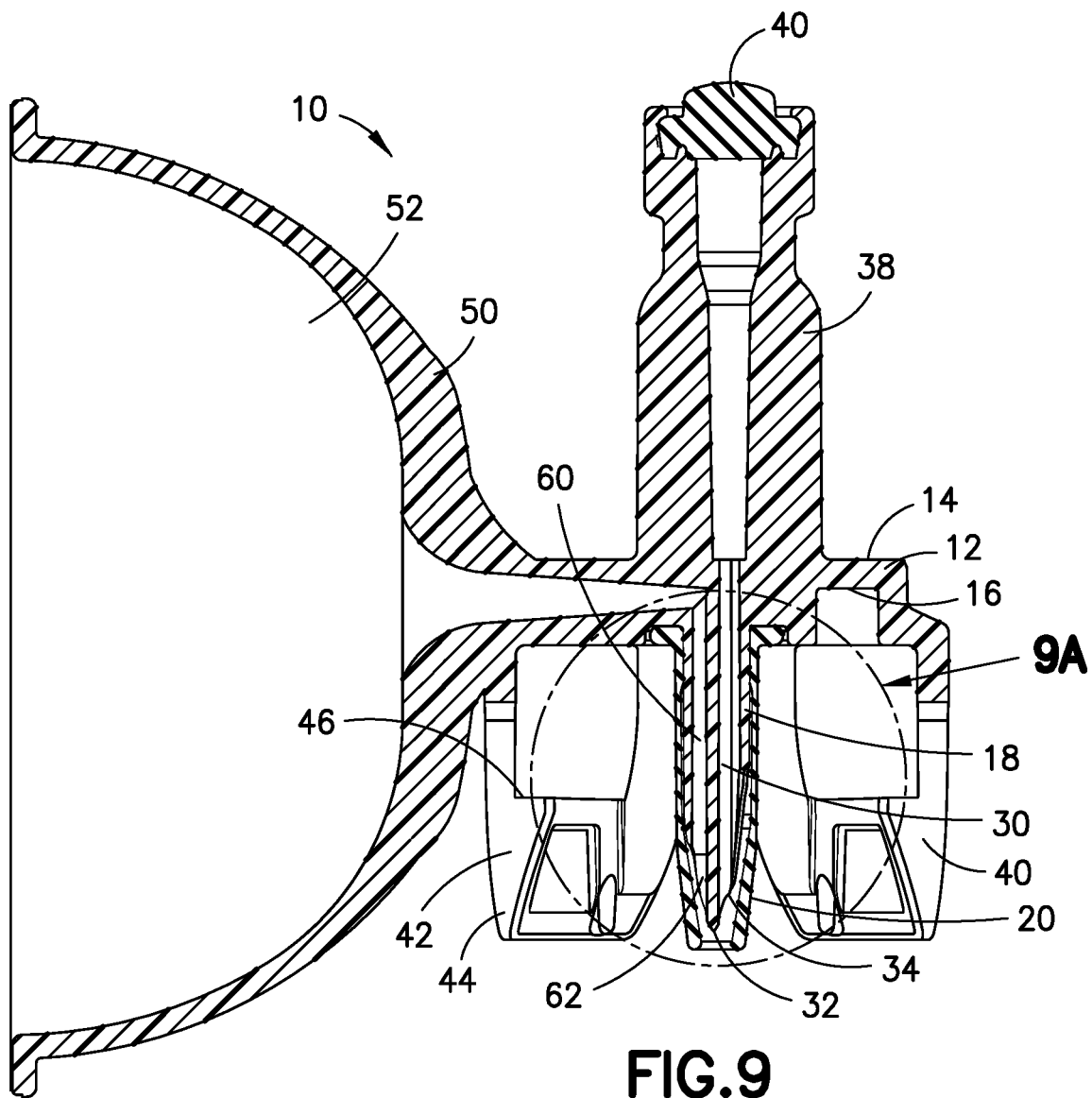
FIG. 9 is a cross-sectional view taken along line 9-9 in FIG. 6 according to one embodiment of the present invention.
Figure 10:
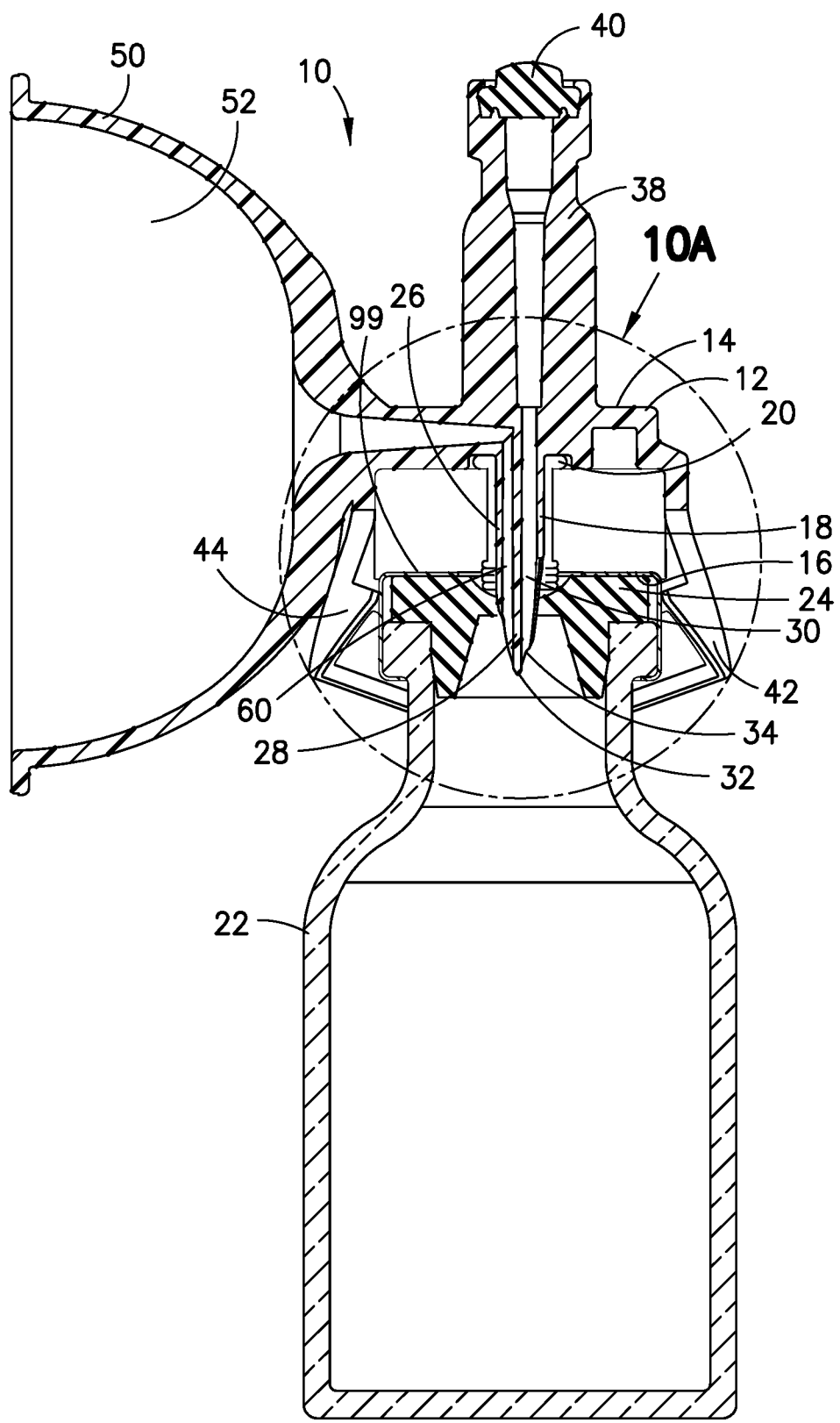
FIG. 10 is a cross-sectional view of the device of FIG. 1 according to one embodiment of the present invention, showing the device in the process of accessing and being attached to a container.

Referring to FIGS. 1-11A, a container access device 10 includes a body 12 having a first side 14 and a second side 16, a piercing member 18 extending from the second side 16 of the body 12, and a retractable sleeve 20 surrounding the piercing member 18. The container access device 10 is configured to transfer fluid from a fluid container 22 having a sealing member 24, which is shown in FIG. 10. The fluid container 22 may include, but is not limited to, a vial, a bottle, and a bag such as an infusion bag.

Figure 11:
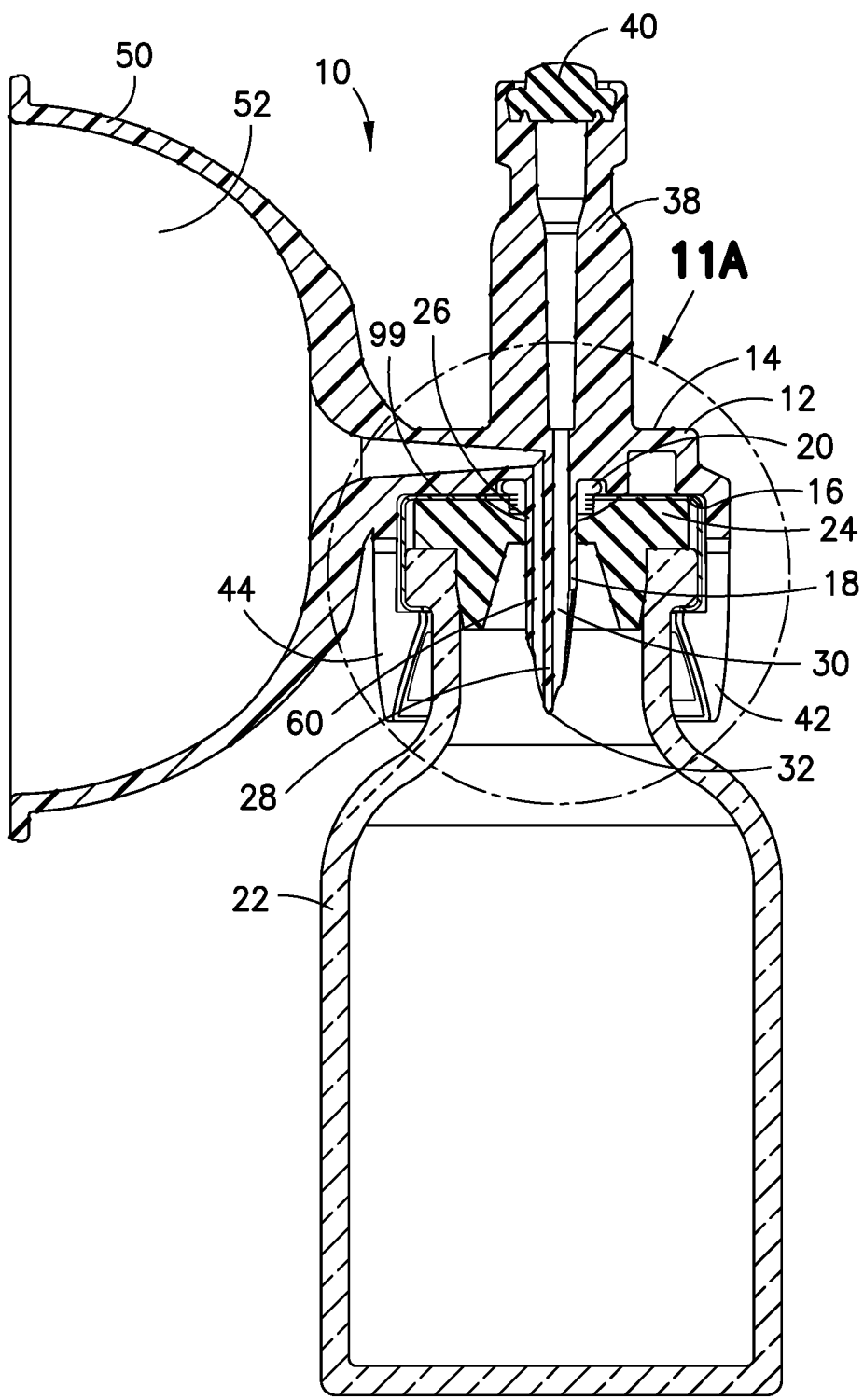
FIG. 11 is a cross-sectional view of the device of FIG. 1 according to one embodiment of the present invention, showing the device accessing a container.

Referring to FIGS. 2-11A, the piercing member 18 has a proximal end 26 and a distal end 28 and defines a longitudinal fluid channel 30. A pointed tip 32 is provided at the distal end 28 for penetrating the sealing member 24 of the container 22. The piercing member 18 has a round cross-section, although other suitable cross-sections may be utilized, including, but not limited to, oval, square, and varying cross-sections. Preferably, the piercing member 18 has a round cross-section to provide a sufficient seal with the sealing member 24 when the device is in use. The piercing member 18 defines a fluid opening 34 in fluid communication with the longitudinal fluid channel 30 that extends from the distal end 28 of the piercing member 18 towards the proximal end 26 of the piercing member 18. The fluid opening 34 can be of any suitable shape, including, but not limited to, rectangular, square, circular, oval, or keyhole. In the embodiments shown in FIGS. 2-11A, the fluid opening 34 is oval-shaped. The fluid opening 34 extends longitudinally along about 50% of the length of the piercing member 18, either from the distal end 28 of the piercing member 18 or a few millimeters from the distal end 28 of the piercing member 18, to ensure that at least part of the fluid opening 34 is located substantially adjacent to an innermost side 36 of the sealing member 24 when the device 10 is in use. The length of the fluid opening 34 can be selected based on the thickness of the thinnest sealing member 24 that it is intended to penetrate and the distance which the piercing member 18 is intended to penetrate the sealing member 24. As shown in FIG. 11, the sealing member 24 overlaps the fluid opening 34 when the device 11 is fully engaged with the container 22. The maximum width of the fluid opening 34 may be equal to at least 20% of the maximum width of the piercing member 18, and is preferably at least 50% of the maximum width of the piercing member 18. The fluid opening 34 may not necessarily extend in a direction parallel or collinear to the longitudinal axis of the device 10 and may extend in a zig-zag pattern along the length of the piercing member 18 or may be defined by a plurality of openings that extend transversely to the longitudinal axis of the device 10.

Figure 10A:
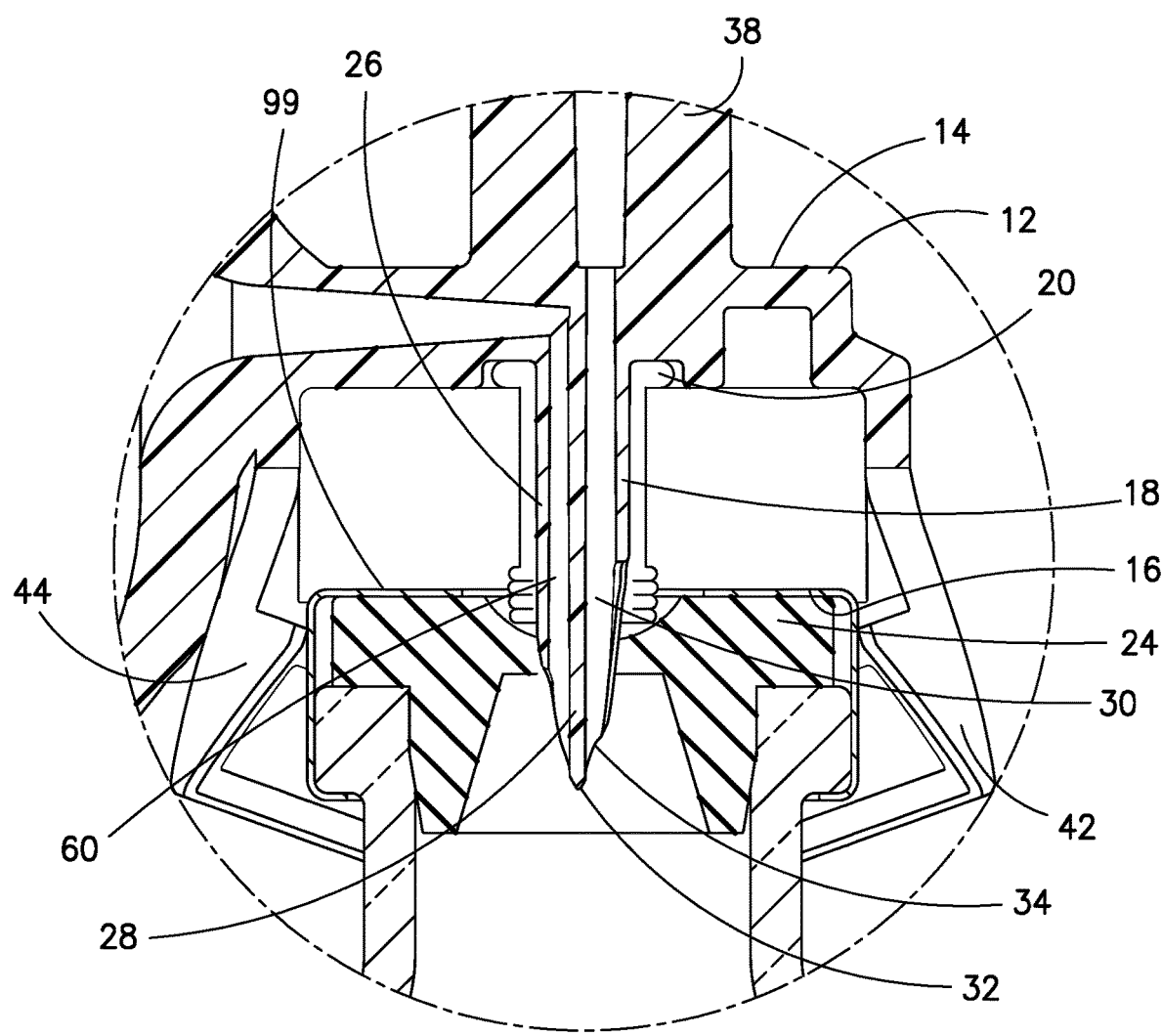
FIG. 10A is an enlarged cross-sectional view of the area indicated in FIG. 10 according to one embodiment of the present invention.
Figure 11A:
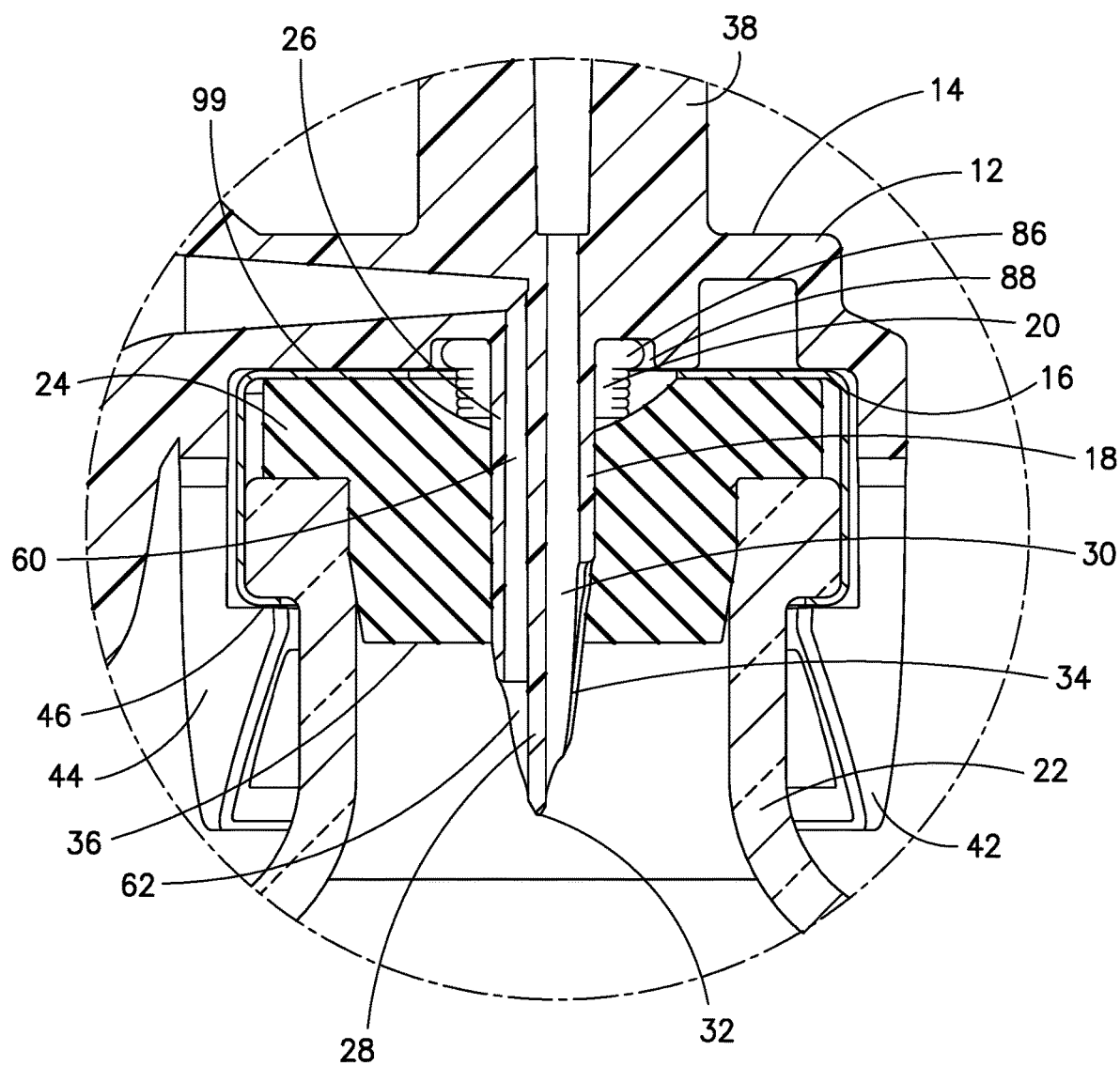
FIG. 11A is an enlarged view of the area indicated in FIG. 11 according to one embodiment of the present invention.

Referring still to FIGS. 2-11A, the body 12 includes a first connecting portion 38 extending from the first side 14 of the body 12. The first connecting portion 38 is configured to attach the device 10 to a syringe adapter or other suitable device or container to allow removal or insertion of fluid into the fluid container 22. As shown in FIG. 9, the first connecting portion 38 is shaped and configured to receive a mating connector, such as a collet arrangement, although other suitable connections may be utilized, including, but not limited to, a luer arrangement, a snap-fit mechanism, a threaded luer lock, and other suitable mechanical or non-mechanical connecting arrangements. The longitudinal fluid channel 30 extends through the body 12 and is in fluid communication with the first connecting portion 38. The first connecting portion 38 may include a septum or membrane 40 to seal the fluid channel 30 at the first connecting portion 38. The body 12 may also include a second connecting portion 42 extending from the second side 16 of the body 12 of the device 10 that is configured to secure the device 10 to the fluid container 22. The second connecting portion 42 includes a plurality of resilient arms 44 having protrusions 46 that engage the rim of the fluid container 22 when the piercing member 18 has been pushed through the sealing member 24 of the fluid container 22, although other suitable arrangements for the second connecting portion 42 may be utilized. As shown in FIGS. 10 and 10A, the resilient arms 44 deflect radially outward when the device 10 is in the process of being attached to the fluid container 22 and return to their original position after being fully secured to the container as shown in FIGS. 11 and 11A.

Referring again to FIGS. 2-11A, the device 10 further includes a pressure equalization arrangement 50 that is configured to equalize the pressure within the container 22 during fluid transfer through the use of an expansible chamber 52. The piercing member 18 defines a longitudinal vent channel 60 and a vent opening 62 extending from the distal end 28 of the piercing member 18 or a few millimeters from the distal end 28 of the piercing member 18 toward the proximal end 26 of the piercing member 18. The vent opening 62 is in fluid communication with the longitudinal vent channel 60. The longitudinal vent channel 60 extends through the body 12 of the device 10 and is in fluid communication with the expansible chamber 52 of the pressure equalization arrangement 50. In particular, during use of the device 10, the longitudinal vent channel 60 and the pressure equalization arrangement 50 is utilized to regulate the pressure within the fluid container 22 and contains the medicament and any vapor thereof within the device 10 and within the fluid container 22. The pressure equalization arrangement 50 may be the balloon or membrane arrangement shown in U.S. Pat. No. 8,523,838, which is hereby incorporated by reference in its entirety, although other suitable pressure equalization arrangements may be utilized, such as, but not limited to, a filtered vent exit. Further, although not shown, the pressure equalization arrangement may include a filter, such as a hydrophobic filter, positioned between the chamber 52 and the longitudinal vent channel 60. The longitudinal fluid channel 30 and longitudinal vent channel 60 may have any suitable cross-section including, but not limited to, round, oval, elliptical, semi-circular, and square. As shown more clearly in FIG. 6A, the cross-sections of the longitudinal fluid channel 30 and longitudinal vent channel 60 are elliptical or semi-circular so that their cross-sectional areas can be maximized within the cylindrical piercing member 18.

Referring FIGS. 2-8A, the piercing member 18 includes first and second flat portions 64, 66 positioned circumferentially between the vent opening 62 and the fluid opening 34 with the first flat portion 64 positioned opposite the second flat portion 66. The first and second flat portions 64, 66 each include a first end 68, 72 and a second end 70, 74. The first and second ends 68, 70, 72, 74 of the flat portions 64, 66 are generally bulbous-shaped with a tapered middle that is narrower than the first and second ends 68, 70, 72, 74. The first and second flat portions 64, 66 are generally planar. The first and second flat portions 64, 66 are configured to reduce the force needed for the piercing member 18 to penetrate the sealing member 24 of the fluid container 22.

Referring to FIGS. 1, 2, 9, and 9A, the retractable sleeve 20 has a distal end 76 and a proximal end 78 and surrounds the piercing member 18. The retractable sleeve 20 may be made from an elastomeric material including, but not limited to, thermoplastic or thermosetting elastomers including, but limited to, silicone rubber. The retractable sleeve 20 has a proximal opening 80 that surrounds the proximal end 26 of the piercing member 18 and a distal opening 82 that is positioned beyond the distal end 28 of the piercing member 18 in the longitudinal direction. Thus, there is a space between the distal opening 82 of the sleeve 20 and the distal end 28 of the piercing member 18. An inner surface of the retractable sleeve 20 has a shape approximating the shape of the outer surface of the piercing member 18. A gap 84 is defined between the inner surface of the retractable sleeve 20 and the outer surface of the piercing member 18. The gap 84 may have a substantially uniform width, i.e., the distance between the inner surface of the retractable sleeve 20 and the outer surface of the piercing member 18 is substantially uniform. The distal opening 82 of the retractable sleeve 20 is in fluid communication with the gap 84 so that sterilizing gases or liquids, such as EtO gas, can enter the gap 84 to sterilize both the inner surface of the retractable sleeve 20 and the outer surface of the piercing member 18. A seal is present between the proximal end 78 of the retractable sleeve 20 and the proximal end 26 of the piercing member 18. The mating surfaces of the seal between the proximal end 78 of the retractable sleeve 20 and the proximal end 26 of the piercing member 18 are never exposed to the atmosphere even during use of the device 10.

Figure 9A:
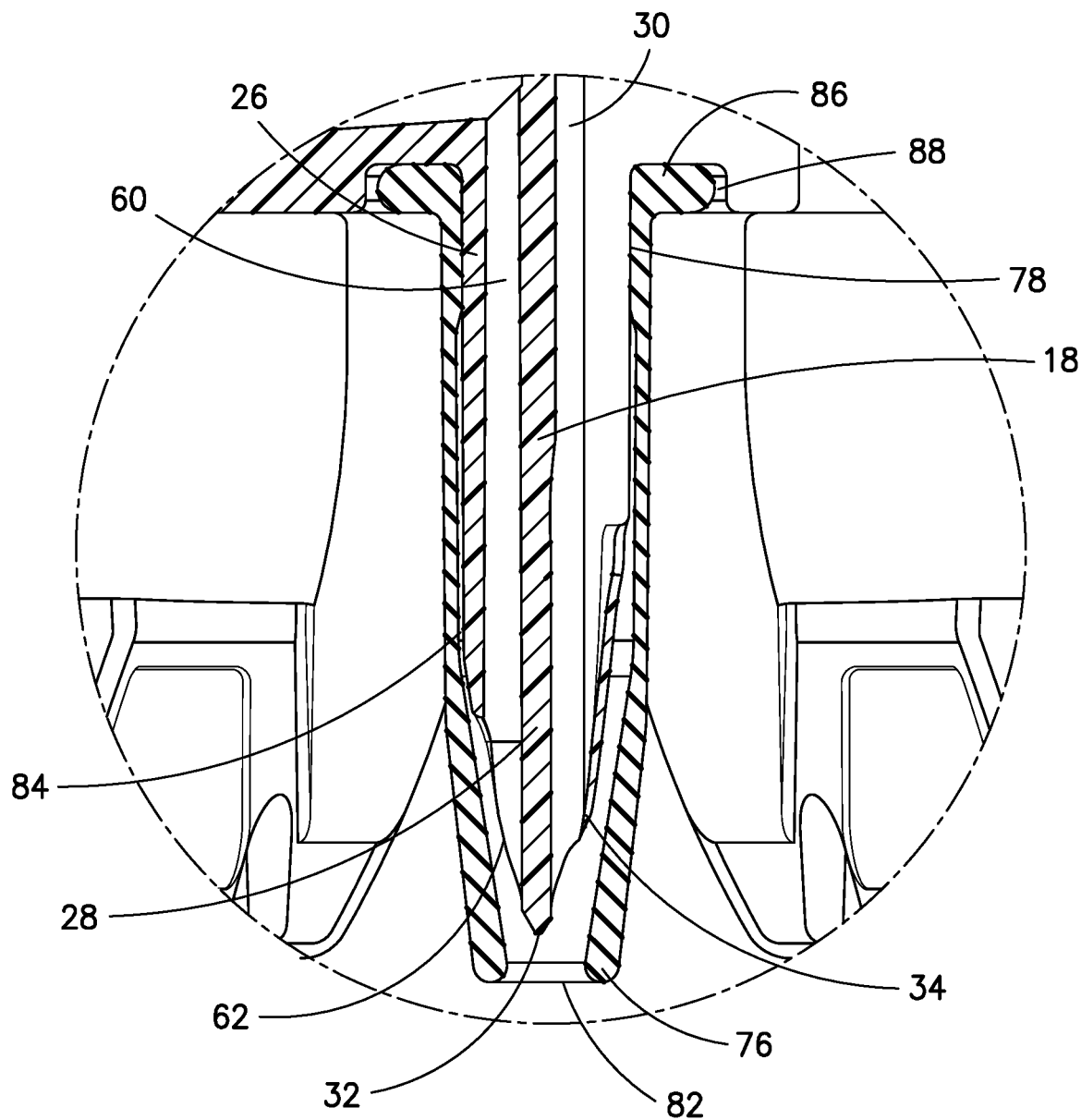
FIG. 9A is an enlarged view of the area indicated in FIG. 9 according to one embodiment of the present invention.

Referring to FIGS. 9 and 9A, the seal between the retractable sleeve 20 and the piercing member 18 may be formed by an interference fit between the proximal end 78 of the retractable sleeve 20 and the proximal end 26 of the piercing member 18. The interference fit may be accomplished by increasing the cross-sectional thickness of the retractable sleeve 20 at its proximal end 78. The retractable sleeve 20 may also be provided with a lip 86 at the proximal end 78. This lip 86 is configured to abut the second side 16 of the body 12 and may be accommodated by an annular groove 88 defined by the body 12 of the device 10. The lip 86 allows the retractable sleeve 20 to be easily assembled over the piercing member 18 by placing the retractable sleeve 20 into a rigid tubular tool such that an end of the tool abuts the lip 86. The tool can then be used to push the retractable sleeve 20 onto the piercing member 18.

Figure 12:
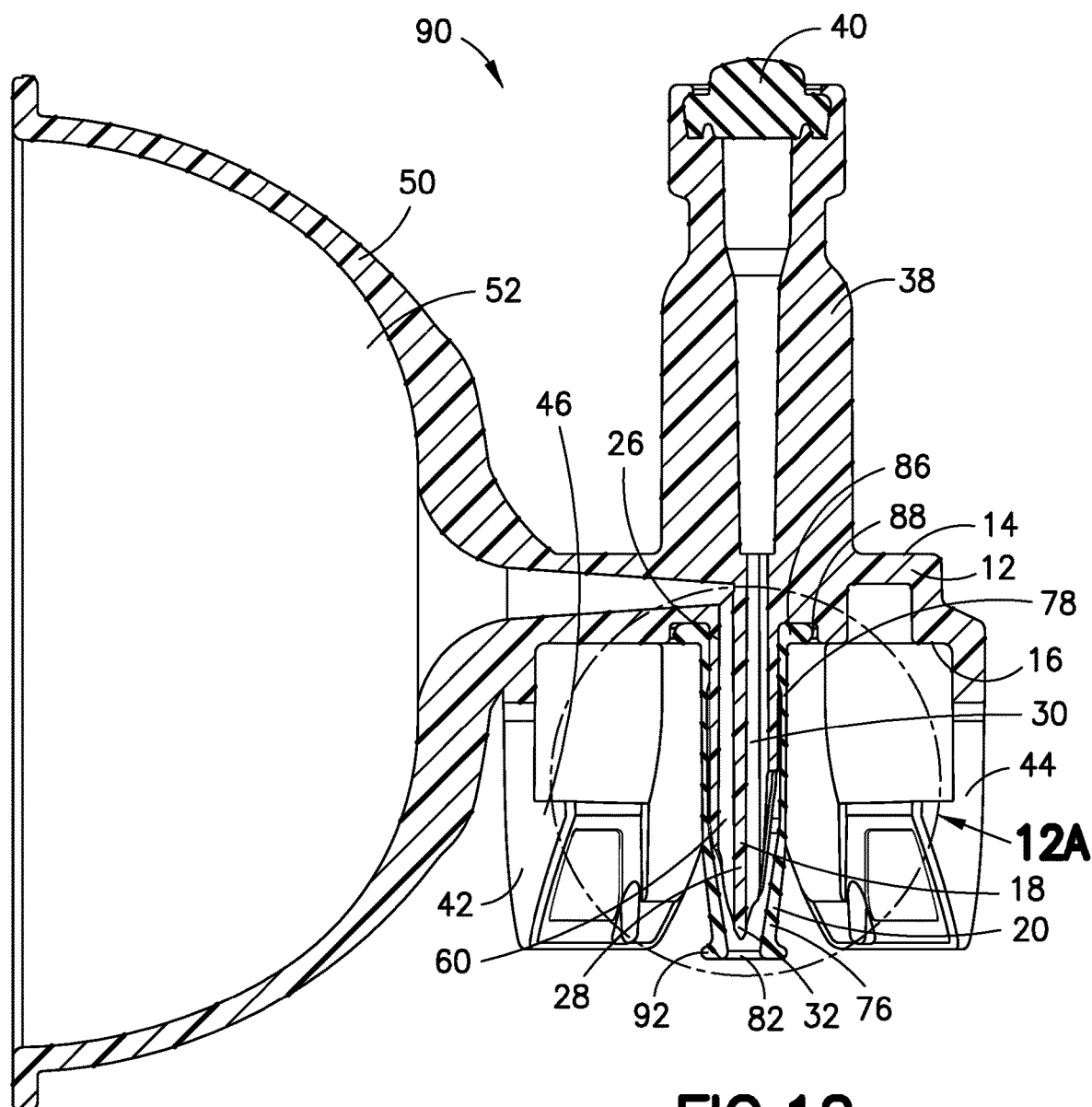
FIG. 12 is a cross-sectional view of a container access device according to a second embodiment of the present invention.
Figure 12A:
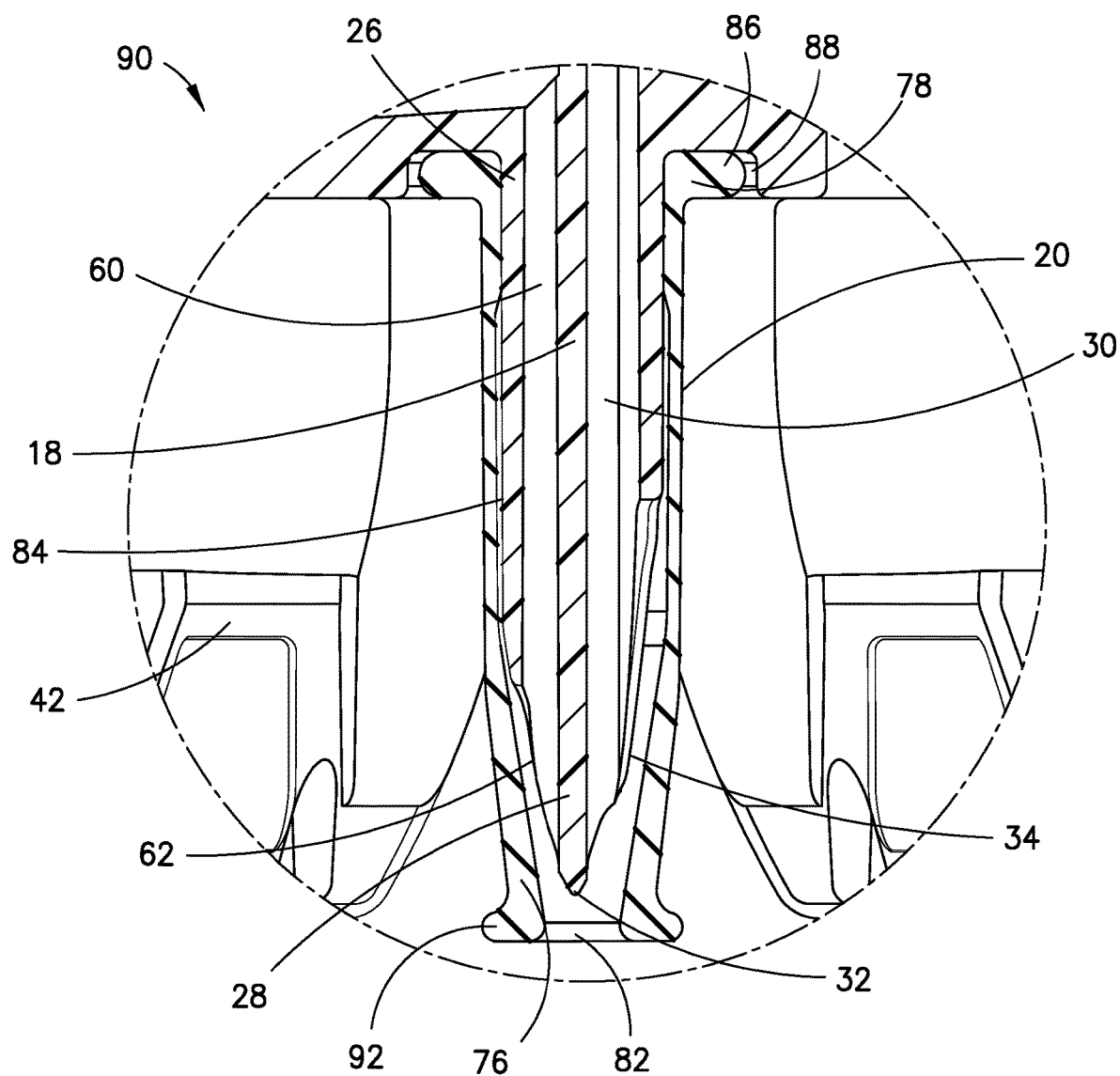
FIG. 12A is an enlarged view of the area indicated in FIG. 12 according to one embodiment of the present invention.

Referring to FIGS. 12 and 12A, a further embodiment of a container access device 90 is shown. The device 90 is similar to the device 10 shown in FIGS. 1-11A and like reference numbers are used for like elements. The device 90 shown in FIG. 12, however, includes a lip 92 adjacent the distal opening 82 in order to provide a better seal with the sealing member 24 of the fluid container 22 when the device 10 is in use.

Figure 13:
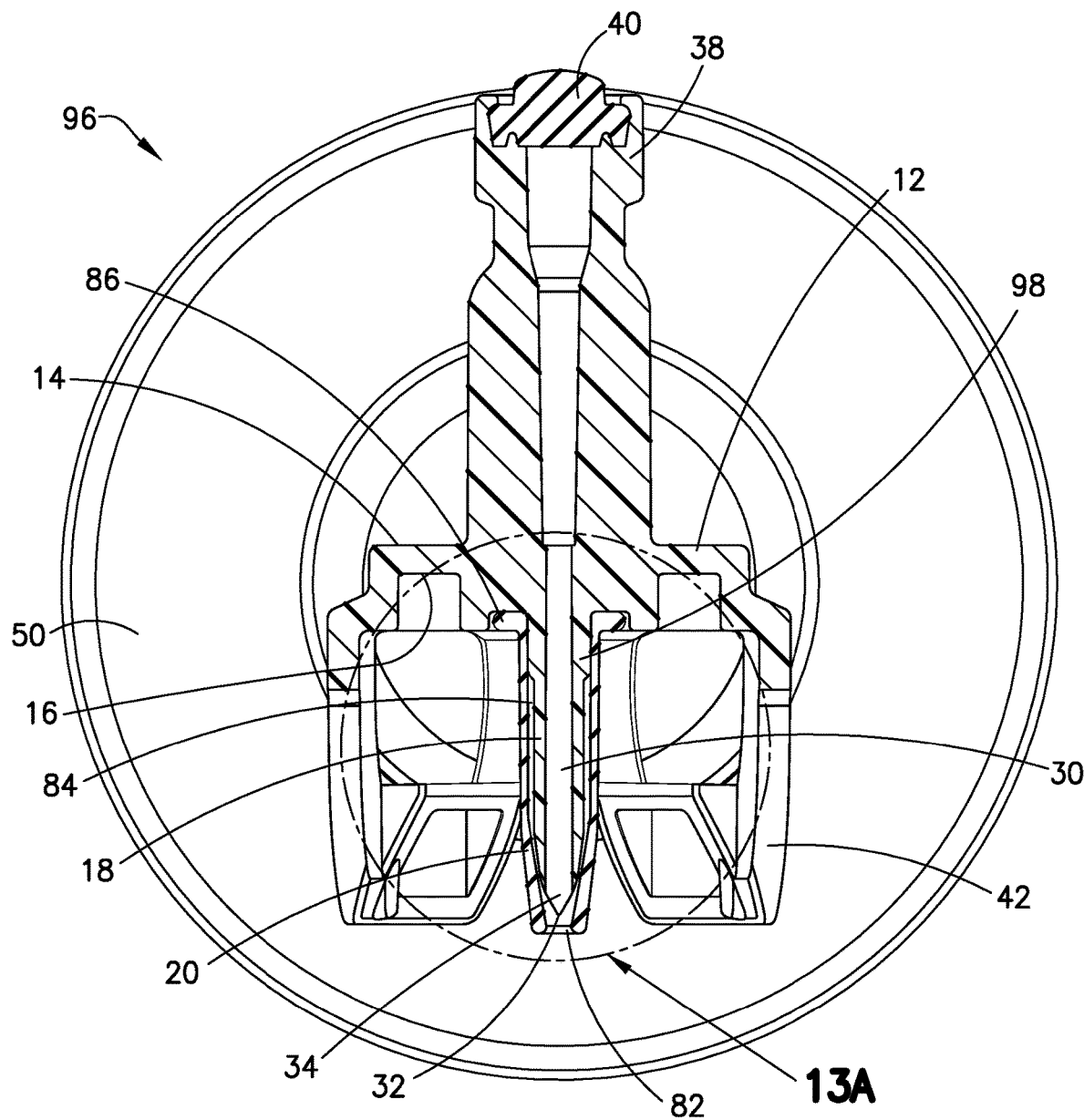
FIG. 13 is a cross-sectional view of a container access device according to a third embodiment of the present invention.
Figure 13A:
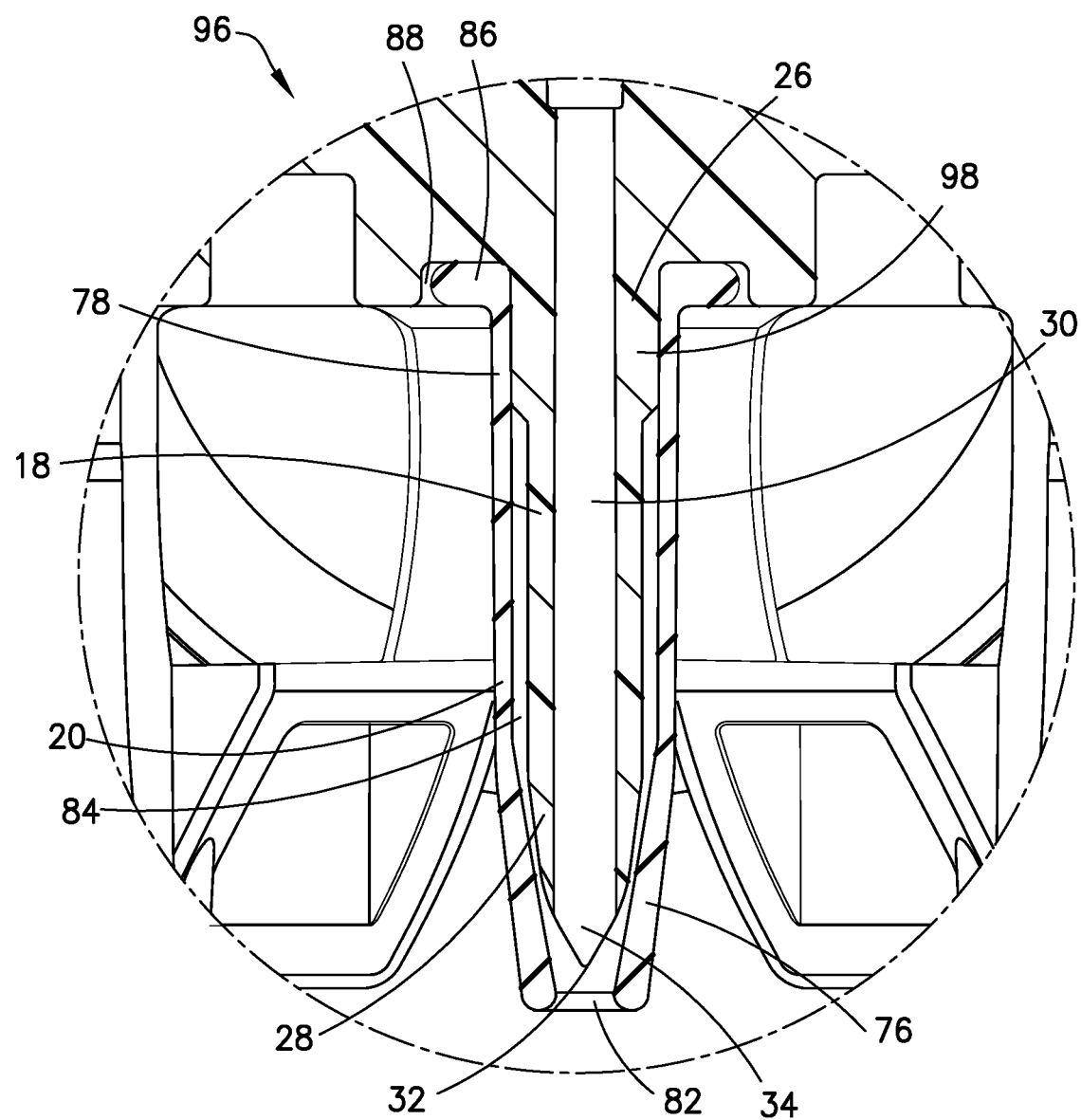
FIG. 13A is an enlarged view of the area indicated in FIG. 13 according to one embodiment of the present invention.

Referring to FIGS. 13 and 13A, another embodiment of a container access device 96 is shown. The device 96 is similar to the device 10 shown in FIGS. 1-11A and like reference numbers are used for like elements. The device 96 in FIG. 13, however, obtains an interference fit between the retractable sleeve 20 and the piercing member 18 by increasing the thickness of a portion 98 of the piercing member 18 at its proximal end 26. Also, as shown in FIG. 13, the device 96 may only have a longitudinal fluid channel 30 and no vent opening.

Referring again to FIGS. 1, 2, and 9-11A, the retractable sleeve 20 is configured to abut against an outermost side 99 of the sealing member 24 when the device 10 has been inserted into a fluid container 22 and to retract as the piercing member 18 penetrates more deeply into the sealing member 24. When the device 10 is fully inserted into the sealing member 24 of the fluid container 22, as shown in FIG. 11, at least a portion of the fluid opening 34 is exposed to the interior of the fluid container 22 while the remaining portion of the fluid opening 34 is sealed by the sealing member 24 of the fluid container 22, thereby preventing deterioration or contamination of the contents of the fluid container 22 and preventing the contents of the fluid container 22 from leaking out and contaminating the surrounding environment. More specifically, as shown in FIGS. 10 and 10A, as the piercing member 18 is entering the fluid container 22, the fluid opening 34 spans the thickness of the sealing member 24 of the fluid container 22. Without the retractable sleeve 20, toxic vapors or substances could potentially be expelled to the surrounding atmosphere or contaminants could potentially enter into the fluid container 22. The retractable sleeve 20 provides a seal with the sealing member 24 of the fluid container 22 and retracts as the piercing member 18 is inserted into the fluid container 22 to prevent any leakage into or out of the fluid container 22. Further, the elongated size and shape of the fluid opening 34 allows the fluid container 22 to be completely emptied when the fluid container 22 is inverted, which is typical during the withdrawal of medicament from the fluid container 22. If the entirety of the fluid opening 34 were positioned within the fluid container 22, all of the medicament may not be emptied from the fluid container 22 depending on the size of the sealing member 24.

As the piercing member 18 is inserted through the sealing member 24 and into the fluid container 22, the retractable sleeve 20 is compressed between the sealing member 24 and body 12 of the device 10 as shown in FIGS. 10-11A. This forms a seal between the retractable sleeve 20 and the sealing member 24 and between the retractable sleeve 20 and the body 12 of the device 10, thereby assuring that none of the contents of the fluid container 22 is exposed to the atmosphere during transfer of the fluid.

The length of the piercing member 18, the fluid opening 34, and the retractable sleeve 20 may be selected such that several conditions are met when the device 10 is inserted into the sealing member 24 of the fluid container 22. First, a portion of the fluid opening 34 is disposed within the fluid container 22 to allow fluid to flow into or out of the fluid container 22 via the longitudinal fluid channel 30 in the piercing member 18. Second, the retractable sleeve 20 is compressed such that the distal end 76 of the retractable sleeve 20 forms a seal with the sealing member 24 and the proximal end 78 of the retractable sleeve 20 forms a seal with the body 12 of the device 10.

Further, the configuration of the device 10 allows for the last drop of fluid to be withdrawn from a variety of the fluid containers 22 having different configurations and different thickness sealing members 24. At the same time, the configuration of the retractable sleeve 20 assures that access to the fluid container 22 and transfer of the fluid occurs in a sealed manner so that no fluids or gases escape from or enter the system while still allowing the entire system to be sterilized. In particular, the gap 84 between the retractable sleeve 20 and the piercing member 18 allows the piercing member 18 and the inner surface of the retractable sleeve 20 to be sterilized. The retractable sleeve 20 also prevents contact contamination of the piercing member 18 before it is inserted into the fluid container 22.

While certain exemplary embodiments of the present invention have been shown and described herein with reference to certain preferred embodiments thereof, it will be understood by those skilled in the art that various changes in form and details may be made therein without departing from the spirit and scope of the invention.

The invention claimed is:

1. A device for transferring fluids comprising:
a body having a first side and a second side;
a piercing member extending from the second side of the body, the piercing member having a distal end and a proximal end and defining a longitudinal fluid channel; and
at least one opening positioned at the distal end of the piercing member, the at least one opening in fluid communication with the longitudinal fluid channel, wherein the piercing member includes at least one flat portion,
wherein the piercing member includes first and second flat portions provided on different planes, and
wherein the first and second flat portions each extend along a side surface of the piercing member.

2. The device according to claim 1, wherein the piercing member defines a longitudinal vent channel, and wherein the piercing member includes first and second flat portions positioned circumferentially between the longitudinal vent channel and the longitudinal fluid channel, the first flat portion positioned opposite the second flat portion.

3. The device according to claim 2, wherein the first and second flat portions are configured to reduce a penetration force required to pierce a sealing member of a fluid container relative to a piercing member not having the first and second flat portions.

* * * * *